(12) United States Patent
Allen

(10) Patent No.: US 7,854,713 B2
(45) Date of Patent: Dec. 21, 2010

(54) CRANIAL REMOLDING ORTHOSIS

(75) Inventor: Scott E. Allen, 50 S. 900 East, Suite 1, Salt Lake City, UT (US) 84102

(73) Assignee: Scott E. Allen, Salt Lake City, UT (US)

( * ) Notice: Subject to any disclaimer, the term of this patent is extended or adjusted under 35 U.S.C. 154(b) by 0 days.

(21) Appl. No.: 11/839,631

(22) Filed: Aug. 16, 2007

(65) Prior Publication Data

US 2008/0045871 A1 Feb. 21, 2008

Related U.S. Application Data

(60) Provisional application No. 60/838,490, filed on Aug. 17, 2006.

(51) Int. Cl.
*A61F 5/00* (2006.01)
(52) U.S. Cl. .......................................... 602/17
(58) Field of Classification Search ................... 602/17; 128/857; 2/411, 412, 414, 425
See application file for complete search history.

(56) References Cited

U.S. PATENT DOCUMENTS 2,324,420 A * 7/1943 Oestrike ..................... 264/316
3,726,620 A * 4/1973 Morton ........................... 425/2
4,239,106 A * 12/1980 Aileo .......................... 206/223
5,308,312 A * 5/1994 Pomatto et al. ............... 602/17
6,423,019 B1 7/2002 Papay et al.

* cited by examiner

*Primary Examiner*—Patricia M Bianco
*Assistant Examiner*—Camtu T Nguyen
(74) *Attorney, Agent, or Firm*—Austin Rapp & Hardman

(57) ABSTRACT

A cranial orthosis may be used to re-shape a child's cranium. The cranial orthosis includes an inner layer and a resistance piece. The inner layer is made of silicone and grips the patient's head such that the inner layer does not move once it is positioned on the child's head. The resistance piece encircles the inner layer and is made of plastic. The resistance piece may not contact the patient's head. The resistance piece is attached to the inner layer. The resistance piece provides the necessary resistance that shapes the patient's head into the desired shape. An attachment feature may be added to the inner layer. The attachment feature engages openings on the resistance piece to connect the resistance piece to the inner layer. The resistance piece may also include one or more areas of increased width that provide additional support to the patient's head.

6 Claims, 3 Drawing Sheets

CRANIAL REMOLDING ORTHOSIS

CROSS-REFERENCED RELATED APPLICATIONS

This application claims the benefit of U.S. Provisional Application No. 60/838,490, filed Aug. 17, 2006. This prior provisional application is expressly incorporated herein by reference.

BACKGROUND OF THE INVENTION

It is known in the medical field that infants and children often must wear helmets or a device to help shape their skull or cranium. These devices are sometimes used when the child's skull or cranium has been deformed or misshaped. Accordingly, an orthopedic device, which may be a cranial orthosis, is sometimes used to re-shape the child's cranium or skull.

One of the known problems associated with the known orthopedic devices is that, once placed upon the child, these devices can shift or move on the child's head. Obviously, such movement of the device is undesirable and may hinder the device's ability to re-shape the child's head properly.

Further, known devices have the drawback that they require an expenditure of significant time and energy to fit the device to the child. Often this requires casting the child's head in plaster of paris or using a scanner machine (or hand scanner) to make a model of the child's head. Often, such difficult "sizing" procedures can be traumatic for the child. Moreover, these sizing procedures can take long periods of time. As such, with current technology it requires a few days or even a few weeks to fit the child and construct the appropriate cranial orthosis.

Finally, current devices for cranial orthosis cannot grow as the child grows. Rather, as the child increases in size, a new device must be constructed. Of course, the procurement of this new device is costly and time consuming.

Accordingly, there is a need in the art for a new type of cranial orthosis device which address one or more of the above-referenced problems. Such a device is disclosed herein.

BRIEF SUMMARY OF THE INVENTION

The present embodiments relate to a new type of cranial orthosis device that is designed to re-shape a child's skull in the event that the child's skull or cranium is misshaped. The cranial orthosis comprise two elements or pieces, namely an inner layer and a resistance piece. The inner layer may be constructed of silicone whereas the resistance piece is made of a plastic. This inner layer may be molded and shaped such that it fits onto and grips the patient's head. Once the inner layer has been properly positioned, it will not move or shift on the child's cranium. In other words, the inner layer will not move relative to the patient's head.

The inner layer is soft or flexible enough to allow for growth of the child's cranium in certain areas. Specifically, as the cranium grows, the inner layer will stretch and accommodate this growth.

The inner layer may have a plurality of attachment features. These attachment features are designed to connect the inner layer to the resistance piece. In some embodiments, these attachment features will be tabs, extensions, or other features that extend from the inner layer. The resistance piece may include one or more openings. The attachment features may engage the openings.

The resistance piece is made of a stiffer, firmer material than the inner layer. Accordingly, the resistance piece provides the necessary resistance to re-shape the child's cranium. It is the support and pressure placed on the cranium by the resistance piece that operates to reshape the head. The resistance may also include one or more areas of increased width which may provide specific resistance to improper growth of the child's head at particular locations.

As the child grows, the resistance piece can also be modified. This may occur by trimming or heating of the plastic material, thereby causing the material to stretch, expand, or change shape. In other embodiments, the desired adjustment of the resistance piece may occur by simply replacing the old resistance piece with a new piece that is more accurately shaped/fitted to provide the desired cranium re-shaping.

It should be noted that both the inner layer and the resistance piece may be formed by injection molding. Those skilled in the art would appreciate how such injection molding may be accomplished. Other manufacturing/production methods for the inner layer and/or the resistance piece may also be used.

BRIEF DESCRIPTION OF THE SEVERAL VIEWS OF THE DRAWINGS

In order to readily understand the manner in which the above-recited and other features and advantages of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

The presently preferred embodiments of the present invention will be best understood by reference to the drawings, wherein like parts are designated by like numerals throughout. It will be readily understood that the components of the present invention, as generally described and illustrated in the figures herein, could be arranged and designed in a wide variety of different configurations. Thus, the following more detailed description of the embodiments of the present invention, as represented in the Figures, is not intended to limit the scope of the invention, as claimed, but is merely representative of presently preferred embodiments of the invention.

Figure 1:
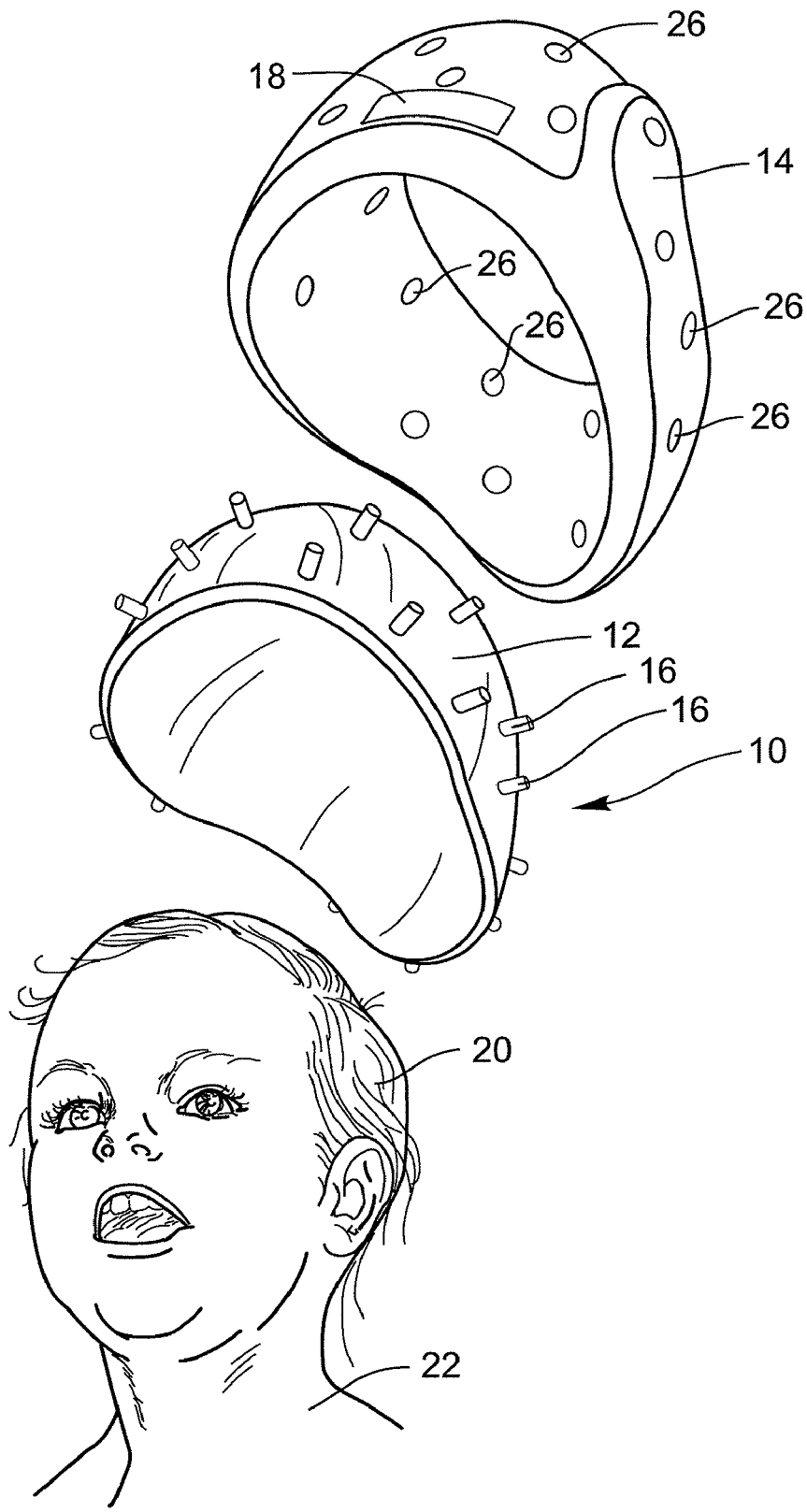
FIG. 1 is an assembly view that illustrates a cranial orthosis according to the present embodiments.

FIG. 1 is an assembly view of a cranial orthosis 10 according to the present embodiments. As explained above, a cranial orthosis 10 is a device that is designed to be worn by a child or infant in the event that a doctor needs to help shape (or reshape) the patient's skull or cranium. Specifically, if the child's skull or cranium has been deformed or misshaped, an orthopedic device is used to re-shape the child's cranium or skull. The cranial orthosis 10 is a device that is capable of providing such re-shaping of the child's skull.

The cranial orthosis may comprise an inner layer 12. The inner layer 12 is designed such that it may be positioned on the head/skull/cranium 20 of the patient 22. The inner layer 12 may generally resemble a swimming cap (or other type of head cap). The inner layer 12 may be constructed of a silicone material. Other materials may also be used. This inner layer 12 may be molded and shaped such that it fits onto the patient's head 20. More specifically, the inner layer 12 may be designed such that when positioned on the patient's cranium 20 or head, the inner layer 12 grips the head 20.

Another material which may be a preferred material for the inner layer 12 is called TPE. This material is a silicone like material which has a transparent property equal to water so when it is combined with the surlyn plastic (which is transparent) the infants head will be able to be viewed through both so as to help avoid skin irritation or possible sores from too much pressure. Other materials may also be used for the inner layer 12. In fact, any flexible material with similar properties as silicone or rubber can be used for the inner layer 12.

Because of such gripping, once the inner layer 12 has been properly positioned, it will not move or shift on the child's head 20. Rather, the inner layer 12 is held in the specified place—i.e., in the location the doctor/clinician has selected to provide optimal shaping or reshaping of the cranium 20. As explained above, one of the problems with known cranial orthosis devices is that these devices have a tendency to move or shift on the child's head 20, especially if the child is active, involved in outdoor or athletic activities, etc. Thus, by having the inner layer 12 grip the child's head 20, this problem is avoided.

As noted above, the inner layer 12 may be constructed out of a silicone material that may be molded into a variety of sizes and shapes. Silicone materials are flexible materials that may be stretched and/or may flex to accommodate a particular child's head 20 (or head shape). Accordingly, embodiments may be constructed in which the inner layer 12 is an "off-the-shelf" item that is pre-molded/pre-formed into shapes and sizes common to children/infants needing a cranial orthosis. The parent/clinician will simply select the size and shape of the "off-the-shelf" inner layer 12 that is closest to the size/shape of the child's cranium and then stretch, flex, or otherwise adjust the silicone inner layer 12, as needed, to conform this product specifically to the child's cranium 20. Generally, cranial orthosis devices are fit to a child's head 20 by having the child undergo a traumatic head scanning procedure (such as placing the child's head 20 in plaster or using an electronic scanner on the child's head 20). However, using the present embodiments, it is possible to obtain the inner layer 12 and have it be shaped specifically to conform to the child's head 20, without subjecting the child to a traumatic experience of having his or her head scanned or cast in plaster.

Of course, further embodiments may be designed in which the child's head/cranium 20 is measured or scanned and then a particular inner layer 12 is molded out of silicone specifically so that it will fit and conform to the child's head 20 size and shape.

Another advantage of using a flexible material, such as silicone, for the inner layer 12 is that the flexible material is soft enough to allow for growth of the child's cranium 20 in certain areas. Specifically, as the cranium grows, the inner layer 12 will stretch and accommodate this growth. That way, the child will not have to obtain another orthosis devices as he or she grows. Of course, if the child truly does outgrow the inner layer 12, a new inner layer 12 may easily be obtained.

The inner layer 12 may have a plurality of attachment features 16. These attachment features 16 are designed to connect the inner layer 12 to a resistance piece 14. In some embodiments, these attachment features 16 will be tabs, extensions, or other features that extend from the inner layer 12. The resistance piece 14 may include one or more openings 26. Specifically, in certain embodiments, the openings are sized and designed such that the attachment features 16 engage, engage and pass through, or fit into the openings 26, as illustrated, for example, in FIG. 2D. Of course, those skilled in the art will recognize that having the attachment features 16 fit into openings 26 is but one example of how the inner layer 12 may be attached to the resistance piece 14. Any type of engagement or mechanism for engaging the resistance piece 14 with the inner layer 12 may be used.

The resistance piece 14 will now be discussed in detail. The resistance piece 14 may be constructed of a plastic or plastic material, such as surlyn plastic (or another similar plastic). Any type of plastic material may be used for the resistance piece 14. This resistance piece 14 provides firm resistance to the growth of the cranium 20 in areas of needed restriction. The resistance piece 14 is shielded from contacting the skin via the inner layer 12. In some embodiments, the resistance piece 14 encircles the inner layer 12.

The resistance piece 14 is made of a stiffer, firmer material than the inner layer 12. Accordingly, the resistance piece 14 provides the necessary resistance to re-shape the child's cranium 20. More specifically, the resistance piece 14 provides firm resistance to the growth of the cranium 20 in the areas of needed restriction. It is the support and pressure placed on the cranium 20 by the resistance piece 14 that operates to reshape the head. It should be noted that the resistance piece 14 does not need to encompass and/or be suspended on the cranium of the child. Rather, the resistance piece 14 may be simply added over the inner layer 12. In other embodiments, the resistance piece 14 may simply be one or more attachments which are added to the inner layer 12 to provide the support in the necessary locations. Any shape or feature capable of providing resistance to the child's head may be used as the resistance piece 14.

The resistance piece 14 may also include one or more areas of increased width 18 which may provide specific resistance to improper growth of the child's head at particular locations. These further areas allow the clinician to further tailor the re-shaping ability of the resistance piece, as needed.

The resistance piece 14 can be made in predetermined sizes and shapes. Thus, like the inner layer 12, the resistance piece 14 may be an "off-the-shelf" item that is purchased by the parent/clinician desiring to reshape the child's cranium. The parent/clinician will select the resistance piece 14 that most appropriately allows the cranium to be re-shaped. Since the resistance piece 14 is likewise available "off-the-shelf," unnecessary casting or scanning of the child's head 20 is avoided.

As the child grows, the resistance piece 14 can also be modified. This may occur by trimming or heating of the plastic material, thereby causing the material to stretch, expand, or change shape. In other embodiments, the desired adjustment of the resistance piece 14 may occur by simply replacing the old resistance piece 14 with a new piece 14 that is more accurately shaped/fitted to provide the desired cranium re-shaping.

Referring still to FIG. 1, it is apparent that the present embodiments also relate to a method of providing a cranial orthosis 10 to a patient. This method will involve the steps of obtaining an inner layer 12. This inner layer 12 may be obtained, for example, by purchasing an "off-the-shelf" product or by molding an inner layer 12. The inner layer 12 will be molded, sized, and/or fit such that it matches the size, shape, and configuration of the patient's cranium 20. Once the inner layer 12 has been obtained, the inner layer 12 may be positioned on the patient's head 20. In some embodiments, the positioned inner layer 12 will grip the cranium 20.

A resistance piece 14 will also be obtained. The resistance piece 14 may be made of a harder plastic material. The resistance piece may then be attached to the inner layer 12, wherein the resistance piece 14 provides the necessary resistance that shapes the patient's head into the desired shape. In some embodiments, the inner layer 12 may include one or more attachment features 16 that engage openings 26 on the resistance piece 14.

Figure 2A:
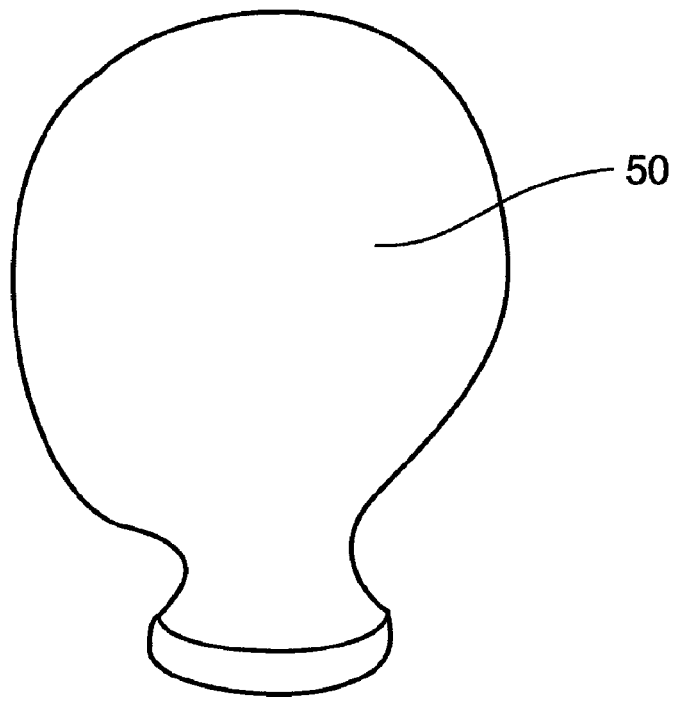
FIGS. 2A through 2C are perspective views that illustrate a method of molding a cranial orthosis.

FIGS. 2A through 2D illustrate one method for molding the cranial orthosis 10. However, those skilled in the art will recognize that this illustration (and the accompanying description) is given for illustrative purposes only. A variety of different molding methods, or methods for creating/forming the cranial orthosis 10, may be used. FIG. 2A shows the mold 50. Specifically, a mold 50 is obtained which has the desired shape of a child's cranium.

Figure 2B:
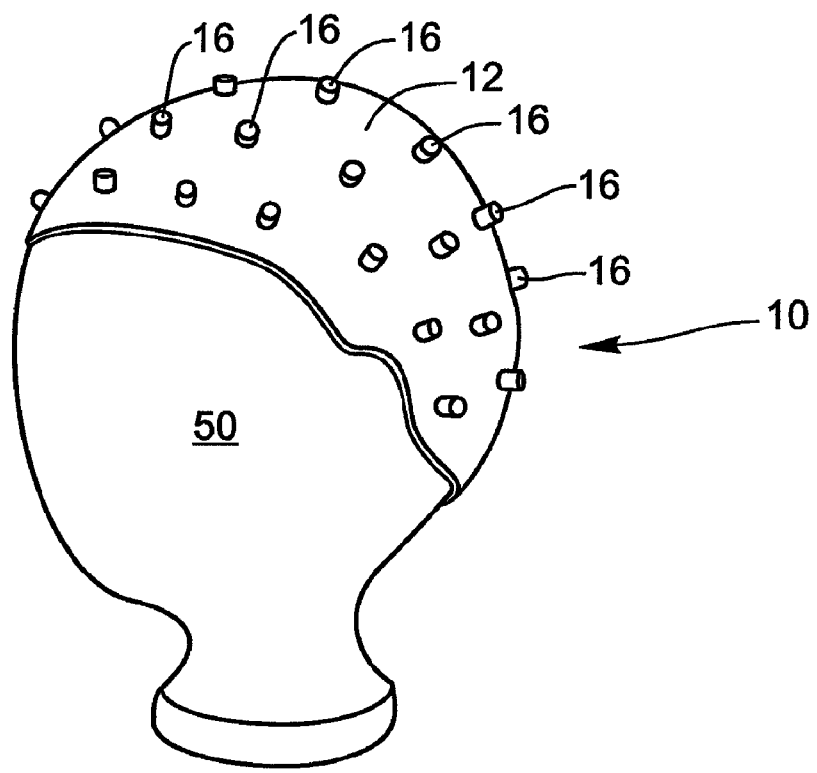

FIG. 2B shows the way in which the inner layer 10 may be molded. To the mold 50, the inner layer 12 is added and formed. As noted above, the inner layer 12 is made of silicone, or other similar material. In general, this layer 12 may be formed or added and then is allowed to harden into the desired form. (Those of skill in the art will recognize that the depiction of the mold 50 as resembling a child's cranium is not limiting. Molds of other shapes and/or configurations may also be used).

Similarly, the attachment features 16 may also be added to the inner layer 12. These attachment features 16 may be molded directly onto the specified location of the inner layer 12. However, in other embodiments, the attachment features 16 will be added, as necessary, via adhesives, gluing, welding, or other attachment mechanisms. In some embodiments, the attachment features 16 may be made of silicone (like the inner layer). However, plastic or other materials may also be used.

Figure 2C:
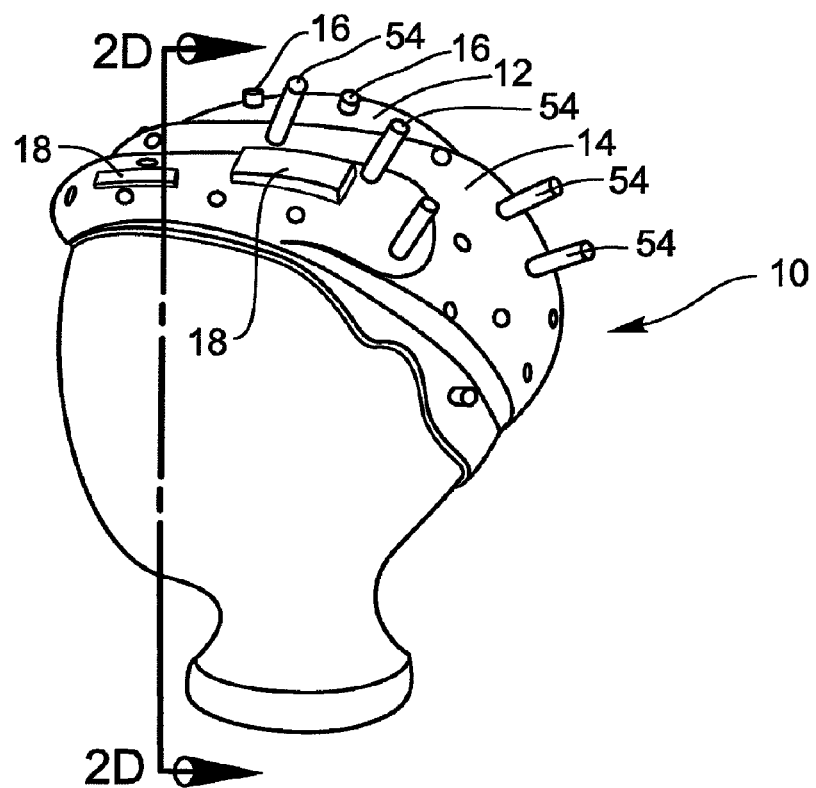

FIG. 2C shows an example of one way in which the resistance piece 14 may be molded or formed. Again, the illustration in FIG. 2C is given for illustrative purposes only. A number of different mechanisms for forming the resistance piece 14 may also be used.

The resistance piece 14 may be molded onto the mold 50. The mold 50 may be the same mold 50 as used in FIG. 2A or may be a different mold as desired. (In other embodiments, simply a circular object having a diameter approximately equal to the diameter of the child's head may be used as the mold). The plastic material used to form the resistance piece 14 may be heated into a liquid form and then applied to the mold 50 and allowed to harden in the desired configuration. As shown in FIG. 2C, one or more metal poles 54 may be positioned on the mold 50 to mark the location of the attachment features 16. The poles 54 are removed after the resistance piece 14 has hardened. When the poles 54 have been removed, one or more openings 26 (shown in FIG. 1) are formed. Thus, by positioning the poles 54 in locations that correspond to the locations of the attachment features 16, the attachment features 16 will be aligned to engage the openings 26 and connect the resistance piece 14 to the inner layer 12.

The poles (which may be made of metal) are arranged so that when the resistance piece 14 is formed, there will be holes in the resistance piece 14. These holes will correspond to the attachment features 16 to allow the inner layer 12 to attach to the resistance piece 14.

Figure 2D:
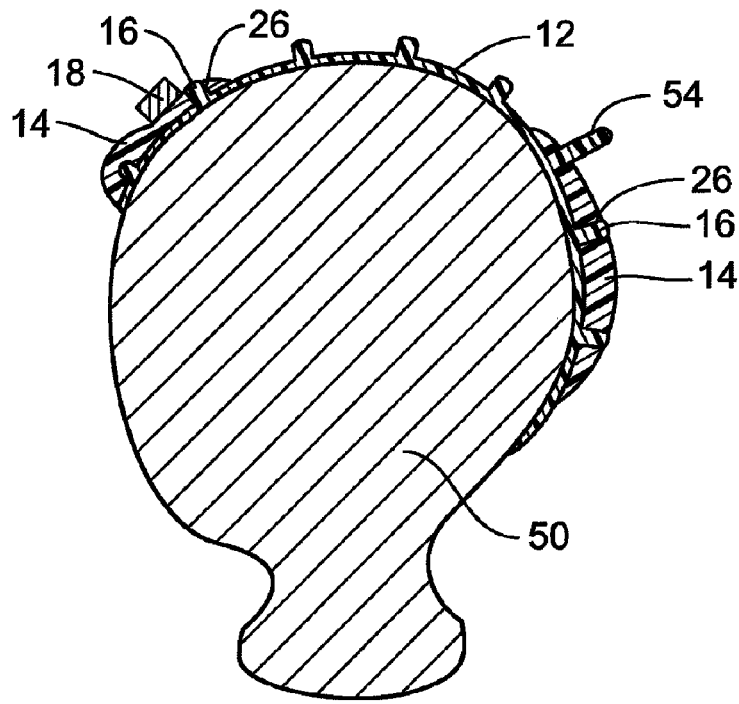
FIG. 2D is a cross-sectional view of FIG. 2C taken along the line 2D-2D.

FIG. 2D is a cross-sectional view taken along the line 2D-2D of FIG. 2C. This cross-sectional view illustrates how the fully assembled orthosis 10 may appear on the mold 50. Once this orthosis 10 is assembled, it may be removed from the mold 50 and added to the child's cranium 20.

FIG. 2D shows that the area 18 is thicker than other areas and may be used to provide additional support in particular areas for re-shaping the skull 20. Of course, the thickness of other areas of the resistance piece 14 may be modified/selected to provide the sufficient resistance to the skull, as desired.

Further, it should also be noted that the position, shape, and location of the attachment features 16 may also be designed and located to provide the desired re-shaping of the cranium 20. Those of skill in the art will appreciate how the shape, location, etc. may be selected to accomplish such re-shaping.

It should be noted that embodiments may be constructed in which the attachment features 16 for connecting the inner layer 12 to the resistance piece 14 can be shapes raised up or added to the inner layer 12 (such as star shapes, triangle shapes, etc.). A corresponding shape may then be added/recessed into the surlyn plastic resistance piece 14, such that the shapes fit together (like a key going into a lock). Other embodiments may be constructed in which the attachment features 16 are added to the resistance piece 14 and the opening 26 or other feature designed to receive the attachment feature 16 is found in the inner layer 12.

Also a further embodiment may be constructed in which there are no separate attachment features 16. Rather, in this embodiment, the rubber texture of the inner layer 12 will grip not only to the child's head, but this texture will also grip the resistance piece 14. Specifically, the resistance piece 14 will apply compression to the rubber material used for the inner layer 12. This compression is caused by the resistance piece 14 restricting the growth of the head, thereby sandwiching the inner layer 12 between the head and the resistance piece 14, and operating to hold the inner layer 12 in the proper position.

Embodiments may be designed in which the inner layer 12 is molded on the mold 50 and allowed to harden. Once this layer has been formed, a separator is added to cover the inner layer 12. After the separator is added, the resistance piece 14 will be molded directly onto the same mold. The purpose of the separator is so that after the resistance piece 14 has hardened, the two pieces may be separated. Again, however, other methods for molding and forming both the resistance piece 14 and the inner layer 12 may also be used.

Those of skill in the art will recognize that the present description also provides a method of forming a cranial orthosis 10 for reshaping a patient's cranium 20. The method involves the step of molding an inner layer 12 from a silicone material. An additional step of providing one or more attachment features 16 on the inner layer 12. These attachment features may be directly molded to the inner layer or may be added subsequently. Further, the method includes molding a resistance piece 14. The resistance piece 14 includes one or more openings 26 that engage the attachment feature 16. The engagement between the attachment feature 16 and the openings 26 operates to connect the inner layer 12 to the resistance piece 14.

Another method of molding the orthosis 10 may be as follows. First, the inner layer 12 is molded and then the resistance piece 14 is molded directly over the inner layer 12. (A separator layer may be positioned between these two layers to ensure that they may be separated). Once this molding has occurred, openings 26 will be added/drilled to the resistance piece 14 at desired locations. Once these openings 26 are added, the attachment features 16 will be added to the layer 12, wherein the position of the features 16 will correspond to the desired position of the openings 26.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A cranial orthosis comprising:
   an inner layer;
   a resistance piece having one or more openings, the resistance piece being attachable to the inner layer, wherein the inner layer includes one or more attachment features that engage and pass through at least one of the openings on the resistance piece when the resistance piece is attached to the inner layer, and wherein the resistance piece provides the necessary resistance that shapes a patient's head into the desired shape when the cranial orthosis is positioned on a patient's head.

2. The cranial orthosis as in claim 1 wherein the inner layer is made of silicone and grips the patient's head such that the inner layer does not move relative to the patient's head when it is positioned on the patient's head.

3. The cranial orthosis as in claim 1 wherein the resistance piece further comprises one or more areas of increased width that provide additional support to the patient's head.

4. The cranial orthosis as in claim 1 wherein the resistance piece encircles the inner layer, wherein the resistance piece is made of plastic.

5. The cranial orthosis as in claim 1 wherein the shape and size of the resistance piece may be adjusted.

6. The cranial orthosis as in claim 1 wherein the resistance piece does not contact the patient's head when the inner layer is positioned on the patient's head.

* * * * *